United States Patent
Salerno et al.

(10) Patent No.: US 9,953,439 B2
(45) Date of Patent: Apr. 24, 2018

(54) SYSTEMS AND METHODS FOR THREE-DIMENSIONAL SPIRAL PERFUSION IMAGING

(71) Applicant: UNIVERSITY OF VIRGINIA PATENT FOUNDATION, Charlottesville, VA (US)

(72) Inventors: Michael Salerno, Charlottesville, VA (US); Craig H. Meyer, Charlottesville, VA (US); Xiao Chen, Charlottesville, VA (US); Yang Yang, Charlottesville, VA (US); Frederick H. Epstein, Charlottesville, VA (US); Christopher M. Kramer, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 91 days.

(21) Appl. No.: 14/952,859

(22) Filed: Nov. 25, 2015

(65) Prior Publication Data
US 2016/0148378 A1    May 26, 2016

Related U.S. Application Data

(60) Provisional application No. 62/084,308, filed on Nov. 25, 2014.

(51) Int. Cl.
*G06K 9/00* (2006.01)
*G06T 11/00* (2006.01)
(Continued)

(52) U.S. Cl.
CPC .......... *G06T 11/003* (2013.01); *A61B 5/0044* (2013.01); *A61B 5/0263* (2013.01);
(Continued)

(58) Field of Classification Search
CPC .................. G06T 11/003; G01R 33/5601
See application file for complete search history.

(56) References Cited

U.S. PATENT DOCUMENTS

| | | |
|---|---|---|
| 4,999,580 A | 3/1991 | Meyer et al. |
| 5,233,301 A | 8/1993 | Meyer et al. |

(Continued)

FOREIGN PATENT DOCUMENTS

| | | |
|---|---|---|
| WO | 02084305 A2 | 10/2002 |
| WO | 2012145547 A1 | 10/2012 |
| WO | 2013023214 A1 | 2/2013 |

OTHER PUBLICATIONS

Cernicanu, A. et al., "Theory-based signal calibration with single-point T1 measurements for first-pass quantitative perfusion MRI studies," Acad. Radiol., 2006, pp. 686-693, 13(6), Elsevier, Inc.

(Continued)

*Primary Examiner* — Oneal R Mistry
(74) *Attorney, Agent, or Firm* — Meunier Carlin & Curfman LLC

(57) ABSTRACT

Some aspects of the present disclosure relate to systems and methods for three-dimensional spiral perfusion imaging. In one embodiment, a method for perfusion imaging of a subject includes acquiring perfusion imaging data associated with the heart of a subject. The acquiring includes applying an imaging pulse sequence with a three-dimensional stack-of-spirals trajectory. The method also includes reconstructing perfusion images from the acquired perfusion imaging data. The reconstructing includes parallel imaging and motion-guided compressed sensing. The method also includes determining, from the reconstructed perfusion images, absolute perfusion values based on time-intensity relationships to quantify myocardial blood flow of the heart of the subject, and generating a quantitative volumetric (Continued)

perfusion flow map based on the determined absolute perfusion values.

44 Claims, 8 Drawing Sheets
(4 of 8 Drawing Sheet(s) Filed in Color)

(51) Int. Cl.
    *A61B 5/055*      (2006.01)
    *A61B 5/00*      (2006.01)
    *A61B 5/026*      (2006.01)
    *G01R 33/48*      (2006.01)
    *G01R 33/56*      (2006.01)
    *G01R 33/561*      (2006.01)
    *G01R 33/563*      (2006.01)

(52) U.S. Cl.
    CPC .......... *A61B 5/055* (2013.01); *G01R 33/4826* (2013.01); *G01R 33/5601* (2013.01); *G01R 33/5611* (2013.01); *G01R 33/56366* (2013.01)

(56) References Cited

U.S. PATENT DOCUMENTS

| | | | |
|---|---|---|---|
| 5,402,067 A | 3/1995 | Pauly et al. | |
| 5,427,101 A | 6/1995 | Sachs et al. | |
| 5,485,086 A | 1/1996 | Meyer et al. | |
| 5,539,313 A | 7/1996 | Meyer | |
| 5,617,028 A | 4/1997 | Meyer et al. | |
| 5,650,723 A | 7/1997 | Meyer | |
| 5,957,843 A | 9/1999 | Luk Pat et al. | |
| 6,020,739 A | 2/2000 | Meyer et al. | |
| 7,174,200 B2 | 2/2007 | Salerno et al. | |
| 7,558,612 B2 | 7/2009 | Meyer | |
| 7,583,082 B1 | 9/2009 | Hu et al. | |
| 7,642,777 B1 | 1/2010 | Meyer et al. | |
| 7,888,935 B1 | 2/2011 | Tan et al. | |
| 8,026,720 B1 | 9/2011 | Chen et al. | |
| 8,094,907 B1 | 1/2012 | Meyer et al. | |
| 8,238,634 B1 | 8/2012 | Meyer et al. | |
| 8,306,289 B1 | 11/2012 | Meyer et al. | |
| 8,700,127 B2 | 4/2014 | Salerno et al. | |
| 2003/0193337 A1 | 10/2003 | Meyer | |
| 2008/0015428 A1 | 1/2008 | Epstein et al. | |
| 2010/0191099 A1 | 7/2010 | Salerno et al. | |
| 2011/0223103 A1 | 9/2011 | Beller et al. | |
| 2013/0274592 A1* | 10/2013 | Shin | A61B 5/055 600/420 |
| 2013/0307536 A1 | 11/2013 | Feng et al. | |
| 2014/0219531 A1 | 8/2014 | Epstein et al. | |
| 2015/0077112 A1* | 3/2015 | Otazo | A61B 5/055 324/318 |
| 2015/0192653 A1* | 7/2015 | Sharif | A61B 5/055 600/420 |
| 2016/0048955 A1* | 2/2016 | Carmi | G06T 7/11 382/131 |

OTHER PUBLICATIONS

Chen, X et al. "Motion-Compensated Compressed Sensing for Dynamic Contrast-Enhanced MRI Using Regional Spatiotemporal Sparsity and Region Tracking: Block LOw-rank Sparsity with Motion-Guidance (BLOSM)," Mag. Reson. Med., 2014, pp. 1028-1038, 72(4), Wiley Periodicals, Inc.

Jerosch-Herold, M. et al., "Magnetic Resonance quantification of the myocardial perfusion reserve with a Fermi function model for constrained deconvolution," Med Phys., 1998, pp. 73-84, 25(1).

Jerosch-Herold, M. et al., "Myocardial blood flow quantification with MRI by model independent deconvolution," Med Phys., 2002, pp. 886-897, 29(5).

Jerosch-Herold, M., "Quantification of myocardial perfusion by cardiovascular magnetic resonance," J. Cardiov. Magn. Reson., 2010, pp. 1-16, 12(57).

Lustig, M. et al. Sparse MRI: The Application of Compressed Sensing for Rapid MR Imaging, Mag. Reson. Med., 2007, pp. 1182-1195, 58(6), Wiley-Liss, Inc.

Pruessman, K.P. et al., "SENSE: Sensitivity Encoding for Fast MRI," Mag. Reson. Med., 1999, pp. 952-962, 42(5), Wiley-Liss, Inc.

Shin, T. et al., "Three-dimensional first-pass myocardial perfusion MRI using a stack-of-spirals acquisition," Magn. Reson. Med., 2013, pp. 839-844, 69(3).

Tofts, P.S. et al., "Estimating Kinetic Parameters from Dynamic Contrast-Enhanced T(1)-Weighted MRI of a Diffusable Tracer: Standardized Quantities and Symbols," J. Magn. Reson. Im., 1999, pp. 223-232, 10(3), Wiley-Liss, Inc.

Yang, Y. et al., "Whole-Heart Quantification of Myocardial Perfusion with spiral Pulse Sequences," Proc. Intl. Soc. Mag. Reson. Med., 2013, p. 4573, 21.

* cited by examiner

SYSTEMS AND METHODS FOR THREE-DIMENSIONAL SPIRAL PERFUSION IMAGING

CROSS-REFERENCE TO RELATED APPLICATIONS

This Application claims priority to and benefit under 35 U.S.C. § 119(e) of U.S. Provisional Patent Application Ser. No. 62/084,308 filed Nov. 25, 2014, which is hereby incorporated by reference herein in its entirety as if fully set forth below.

Some references, which may include various patents, patent applications, and publications, are cited in a reference list and discussed in the disclosure provided herein. The citation and/or discussion of such references is provided merely to clarify the description of the present disclosure and is not an admission that any such reference is "prior art" to any aspects of the present disclosure described herein. In terms of notation, "[n]" corresponds to the $n^{th}$ reference in the list. All references cited and discussed in this specification are incorporated herein by reference in their entireties and to the same extent as if each reference was individually incorporated by reference.

BACKGROUND

Multi-slice two-dimensional (2D) first-pass perfusion imaging has generally been used to diagnose cardiac conditions such as coronary artery disease (CAD) ([1]). Three-dimensional (3D) perfusion imaging is an attractive alternative to the 2D multi-slice approach and is advantageous due to its high signal to noise ratio (SNR) and contrast to noise ratio (CNR). Additionally, spiral pulse sequences have multiple advantages for myocardial perfusion imaging, including high acquisition efficiency, high SNR, and robustness to motion. Currently, there is growing clinical interest in obtaining quantitative, observer-independent, and reproducible measures of myocardial perfusion.

It is with respect to these and other considerations that the various embodiments described below are presented.

SUMMARY

Some aspects of the present disclosure relate to systems and methods for 3D spiral perfusion imaging.

In one aspect, the present disclosure relates to a method for perfusion imaging of a subject which, in one embodiment, includes acquiring perfusion imaging data associated with the heart of a subject. The acquiring includes applying an imaging pulse sequence with a three-dimensional stack-of-spirals trajectory. The method also includes reconstructing perfusion images from the acquired perfusion imaging data, wherein the reconstructing comprises parallel imaging and motion-guided compressed sensing. The method also includes determining, from the reconstructed perfusion images, absolute perfusion values based on time-intensity relationships to quantify myocardial blood flow of the heart of the subject, and generating a quantitative volumetric perfusion flow map based on the determined absolute perfusion values.

In another aspect, the present disclosure relates to a system which, in one embodiment, includes a data acquisition device configured to acquire perfusion imaging data associated with the heart of a subject. The acquiring includes applying an imaging pulse sequence with a three-dimensional stack-of-spirals trajectory. The system also includes one or more processors that are configured to perform functions that include reconstructing perfusion images from the acquired perfusion imaging data, wherein the reconstructing comprises parallel imaging and motion-guided compressed sensing, determining, from the reconstructed perfusion images, absolute perfusion values based on time-intensity relationships to quantify myocardial blood flow of the heart of the subject, and generating a quantitative volumetric perfusion flow map based on the determined absolute perfusion values.

In another aspect, the present disclosure relates to a method for magnetic resonance imaging of a subject. In one embodiment, the method includes acquiring magnetic resonance data associated with an area of interest of a subject, wherein the acquiring includes applying an imaging pulse sequence with a three-dimensional stack-of-spirals trajectory. The method also includes reconstructing images corresponding to the area of interest from the acquired magnetic resonance data, wherein the reconstructing includes parallel imaging and motion-guided compressed sensing. The method also includes quantifying, from the reconstructed images, values associated with a physiological activity in the area of interest using time-intensity relationships, and generating, from the quantified values, a quantitative volumetric map representing the physiological activity.

In yet another aspect, the present disclosure relates to a non-transitory computer-readable medium. In one embodiment, the non-transitory computer-readable medium stores instructions that, when executed by one or more processors, cause a computing device to perform functions that include acquiring perfusion imaging data associated with the heart of a subject, wherein the acquiring includes applying an imaging pulse sequence with a three-dimensional stack-of-spirals trajectory. The functions further include reconstructing perfusion images from the acquired perfusion imaging data, wherein the reconstructing includes parallel imaging and motion-guided compressed sensing. The functions further include determining, from the reconstructed perfusion images, absolute perfusion values based on time-intensity relationships to quantify myocardial blood flow of the heart of the subject, and generating a quantitative volumetric perfusion flow map based on the determined absolute perfusion values.

Other aspects and features according to the present disclosure will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale. The patent or application file contains at least one drawing executed in color. Copies of this patent or patent application publication with color drawing(s) will be provided by the Office upon request and payment of the necessary fee.

DETAILED DESCRIPTION

Figure 1:
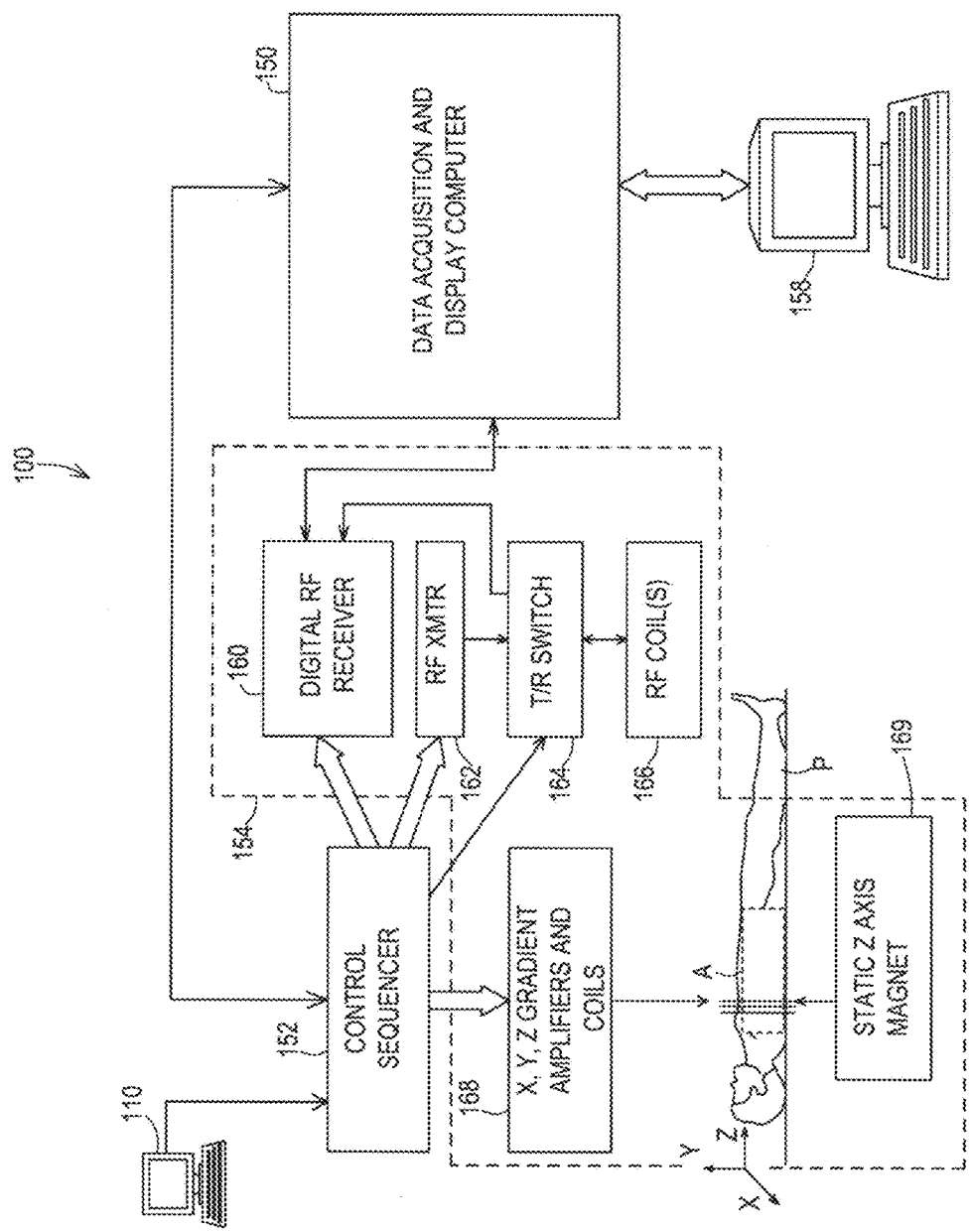
FIG. 1 is a system diagram illustrating an imaging system capable of implementing aspects of the present disclosure in accordance with one or more embodiments.

Some aspects of the present disclosure relate to systems and methods for 3D spiral perfusion imaging. Some embodiments of the present disclosure are directed to 3D whole-heart coverage quantitative first-pass perfusion dual sequence imaging with a stack-of-spirals (SoS) trajectory combined with parallel imaging, compressed sensing (CS) and motion correction to perform robust myocardial blood flow quantification. Some embodiments utilize an accelerated 3D SoS pulse sequence, with parallel imaging and compressed sensing with motion compensation, and an integrated single-shot arterial input function acquisition (AIF) to perform absolute quantification of myocardial perfusion with whole ventricular coverage.

Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

As discussed herein, a "subject" may be any applicable human, animal, or other organism, living or dead, or other biological or molecular structure or chemical environment, and may relate to particular components of the subject, for instance specific tissues or fluids of a subject (e.g., human tissue in a particular area of the body of a living subject), which may be in a particular location of the subject, referred to herein as an "area of interest" or a "region of interest."

A detailed description of aspects of the present disclosure will now be provided with reference to the accompanying drawings. The drawings form a part hereof and show, by way of illustration, specific embodiments or examples. In referring to the drawings, like numerals represent like elements throughout the several figures.

FIG. 1 is a system diagram illustrating an operating environment capable of implementing aspects of the present disclosure in accordance with one or more example embodiments. FIG. 1 illustrates an example of a magnetic resonance imaging (MRI) system 100, including a data acquisition and display computer 150 coupled to an operator console 110, an MRI real-time control sequencer 152, and an MRI subsystem 154. The MRI subsystem 154 may include XYZ magnetic gradient coils and associated amplifiers 168, a static Z-axis magnet 169, a digital RF transmitter 162, a digital RF receiver 160, a transmit/receive switch 164, and RF coil(s) 166. The MRI subsystem 154 may be controlled in real time by control sequencer 152 to generate magnetic and radio frequency fields that stimulate magnetic resonance phenomena in a subject P to be imaged, for example to implement magnetic resonance imaging sequences in accordance with various embodiments of the present disclosure. A contrast-enhanced image of an area of interest A of the subject P (which may also be referred to herein as a "region of interest") may be shown on display 158. The display 158 may be implemented through a variety of output interfaces, including a monitor, printer, or data storage.

The area of interest A corresponds to a region associated with one or more physiological activities in subject P. The area of interest shown in the example embodiment of FIG. 1 corresponds to a chest region of subject P, but it should be recognized and appreciated that the area of interest in various embodiments may encompass various areas of subject P associated with various physiological characteristics, such as, but not limited to the heart region, brain region, upper or lower extremities, or other organs or tissues. Physiological activities that may be evaluated by methods and systems in accordance with various embodiments of the present disclosure may include, but are not limited to, fluid flow such as blood flow, or muscular movement or other conditions.

It should be appreciated that any number and type of computer-based medical imaging systems or components, including various types of commercially available medical imaging systems and components, may be used to practice certain aspects of the present disclosure. Systems as described herein with respect to example embodiments are not intended to be specifically limited to magnetic resonance imaging (MRI) implementations or the particular system shown in FIG. 1.

One or more data acquisition or data collection steps as described herein in accordance with one or more embodiments may include acquiring, collecting, receiving, or otherwise obtaining data such as imaging data corresponding to an area of interest. By way of example, data acquisition or collection may include acquiring data via a data acquisition device, receiving data from an on-site or off-site data acquisition device or from another data collection, storage, or processing device. Similarly, data acquisition or data collection devices of a system in accordance with one or more embodiments of the present disclosure may include any device configured to acquire, collect, or otherwise obtain data, or to receive data from a data acquisition device within the system, an independent data acquisition device located on-site or off-site, or another data collection, storage, or processing device.

Figure 2:
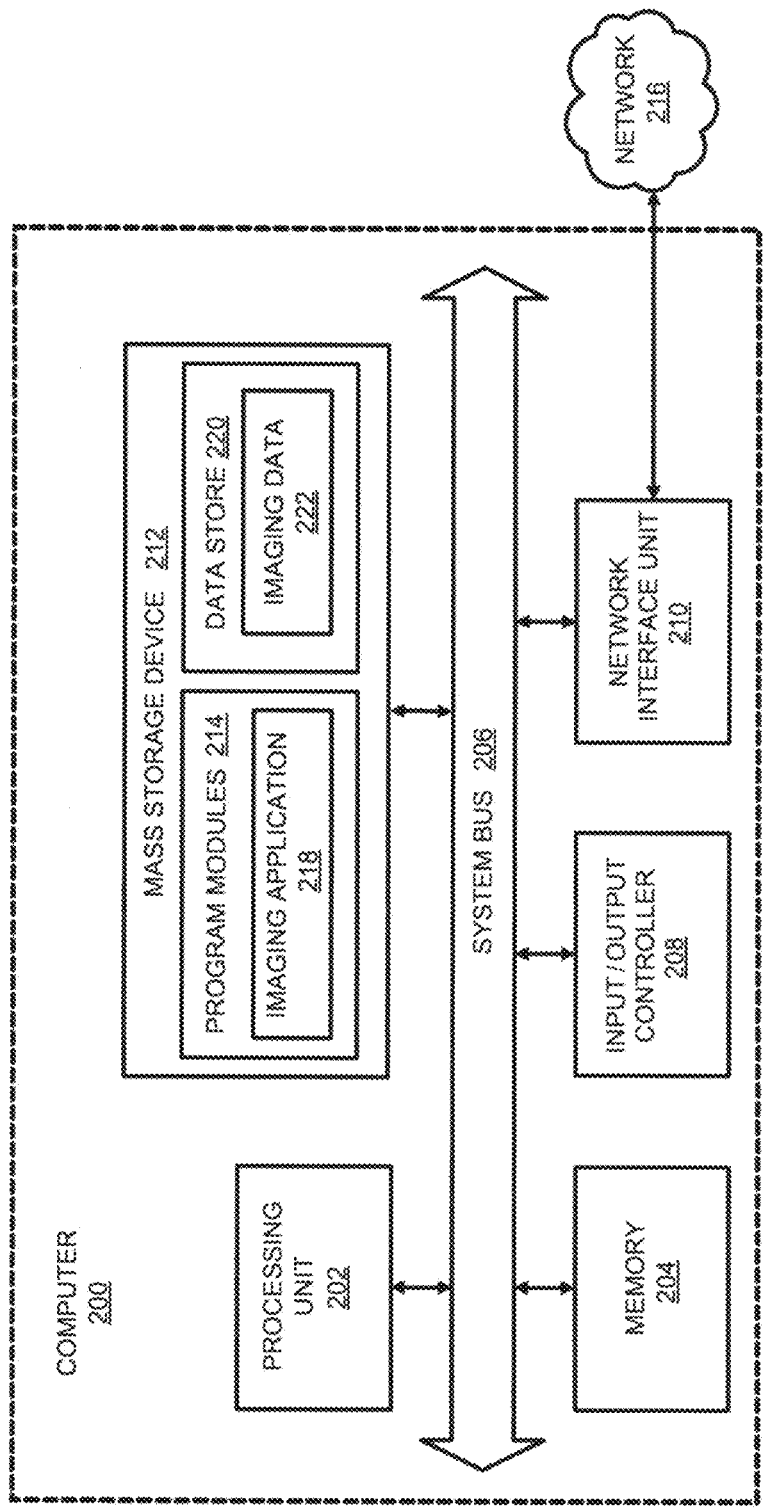
FIG. 2 is a computer architecture diagram showing a general computing system capable of implementing aspects of the present disclosure in accordance with one or more embodiments.

FIG. 2 is a computer architecture diagram showing a general computing system capable of implementing aspects of the present disclosure in accordance with one or more embodiments described herein. A computer 200 may be configured to perform one or more functions associated with embodiments illustrated in one or more of FIGS. 3-9. For example, the computer 200 may be configured to perform operations of the method shown in FIG. 3. It should be appreciated that the computer 200 may be implemented within a single computing device or a computing system formed with multiple connected computing devices. The computer 200 may be configured to perform various distributed computing tasks, in which processing and/or storage resources may be distributed among the multiple devices. The data acquisition and display computer 150 and/or operator console 110 of the system shown in FIG. 1 may include one or more systems and components of the computer 200.

As shown, the computer 200 includes a processing unit 202 ("CPU"), a system memory 204, and a system bus 206 that couples the memory 204 to the CPU 202. The computer 200 further includes a mass storage device 212 for storing program modules 214. The program modules 214 may be operable to perform associated with embodiments illustrated in one or more of FIGS. 3-9 discussed below, for example to cause the computer 200 to perform operations of the method shown in FIG. 3. The program modules 214 may include an imaging application 218 for performing data acquisition and/or processing functions as described herein, for example to acquire and/or process image data corresponding to magnetic resonance imaging of an area of interest. The computer 200 can include a data store 220 for storing data that may include imaging-related data 222 such as acquired data from the implementation of magnetic resonance imaging pulse sequences in accordance with various embodiments of the present disclosure.

The mass storage device 212 is connected to the CPU 202 through a mass storage controller (not shown) connected to the bus 206. The mass storage device 212 and its associated computer-storage media provide non-volatile storage for the computer 200. Although the description of computer-storage media contained herein refers to a mass storage device, such as a hard disk or CD-ROM drive, it should be appreciated by those skilled in the art that computer-storage media can be any available computer storage media that can be accessed by the computer 200.

By way of example and not limitation, computer storage media (also referred to herein as "computer-readable storage medium" or "computer-readable storage media") may include volatile and non-volatile, removable and non-removable media implemented in any method or technology for storage of information such as computer-storage instructions, data structures, program modules, or other data. For example, computer storage media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer 200. "Computer storage media", "computer-readable storage medium" or "computer-readable storage media" as described herein do not include transitory signals.

According to various embodiments, the computer 200 may operate in a networked environment using connections to other local or remote computers through a network 216 via a network interface unit 210 connected to the bus 206. The network interface unit 210 may facilitate connection of the computing device inputs and outputs to one or more suitable networks and/or connections such as a local area network (LAN), a wide area network (WAN), the Internet, a cellular network, a radio frequency (RF) network, a Bluetooth-enabled network, a Wi-Fi enabled network, a satellite-based network, or other wired and/or wireless networks for communication with external devices and/or systems. The computer 200 may also include an input/output controller 208 for receiving and processing input from any of a number of input devices. Input devices may include one or more of keyboards, mice, stylus, touchscreens, microphones, audio capturing devices, and image/video capturing devices. An end user may utilize the input devices to interact with a user interface, for example a graphical user interface, for managing various functions performed by the computer 200. The bus 206 may enable the processing unit 202 to read code and/or data to/from the mass storage device 212 or other computer-storage media. The computer-storage media may represent apparatus in the form of storage elements that are implemented using any suitable technology, including but not limited to semiconductors, magnetic materials, optics, or the like. The computer-storage media may represent memory components, whether characterized as RAM, ROM, flash, or other types of technology. The computer storage media may also represent secondary storage, whether implemented as hard drives or otherwise. Hard drive implementations may be characterized as solid state, or may include rotating media storing magnetically-encoded information. The program modules 214, which include the imaging application 218, may include instructions that, when loaded into the processing unit 202 and executed, cause the computer 200 to provide functions associated with one or more embodiments illustrated in FIGS. 3-9. The program modules 214 may also provide various tools or techniques by which the computer 200 may participate within the overall systems or operating environments using the components, flows, and data structures discussed throughout this description.

In general, the program modules 214 may, when loaded into the processing unit 202 and executed, transform the processing unit 202 and the overall computer 200 from a general-purpose computing system into a special-purpose computing system. The processing unit 202 may be constructed from any number of transistors or other discrete circuit elements, which may individually or collectively assume any number of states. More specifically, the processing unit 202 may operate as a finite-state machine, in response to executable instructions contained within the program modules 214. These computer-executable instructions may transform the processing unit 202 by specifying how the processing unit 202 transitions between states, thereby transforming the transistors or other discrete hardware elements constituting the processing unit 202. Encoding the program modules 214 may also transform the physical structure of the computer-storage media. The specific transformation of physical structure may depend on various factors, in different implementations of this description. Examples of such factors may include, but are not limited to the technology used to implement the computer-storage media, whether the computer storage media are characterized as primary or secondary storage, and the like. For example, if the computer storage media are implemented as semiconductor-based memory, the program modules 214 may transform the physical state of the semiconductor memory, when the software is encoded therein. For example, the program modules 214 may transform the state of transistors, capacitors, or other discrete circuit elements constituting the semiconductor memory.

As another example, the computer storage media may be implemented using magnetic or optical technology. In such implementations, the program modules 214 may transform the physical state of magnetic or optical media, when the software is encoded therein. These transformations may include altering the magnetic characteristics of particular locations within given magnetic media. These transformations may also include altering the physical features or characteristics of particular locations within given optical media, to change the optical characteristics of those locations. Other transformations of physical media are possible without departing from the scope of the present description, with the foregoing examples provided only to facilitate this discussion.

Figure 3:
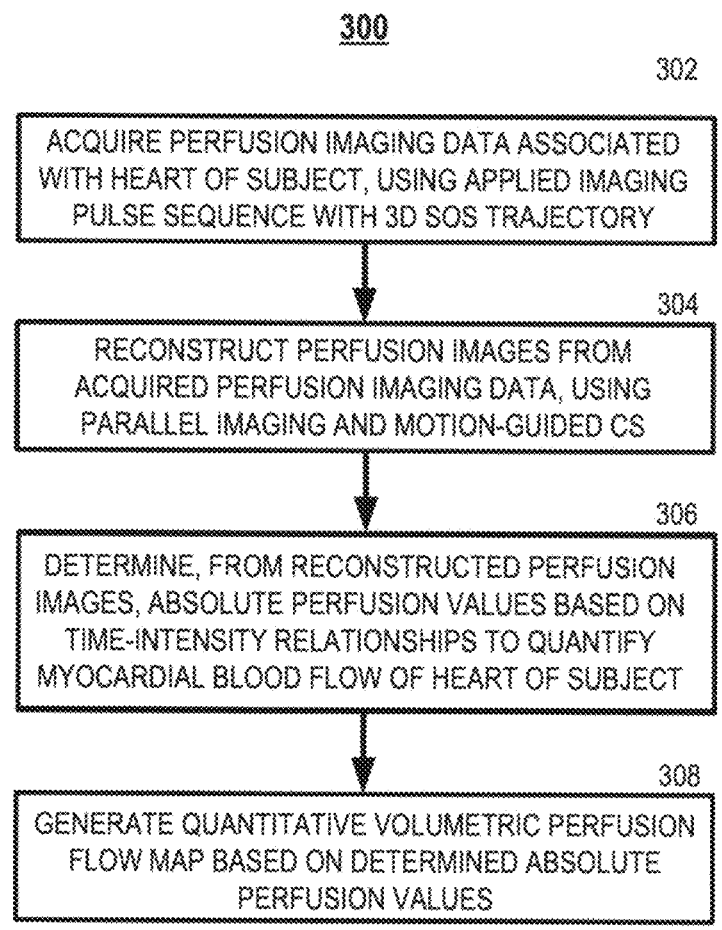
FIG. 3 is a flow diagram illustrating operations of a method for 3D spiral perfusion imaging according to one embodiment of the present disclosure.
Figure 4:
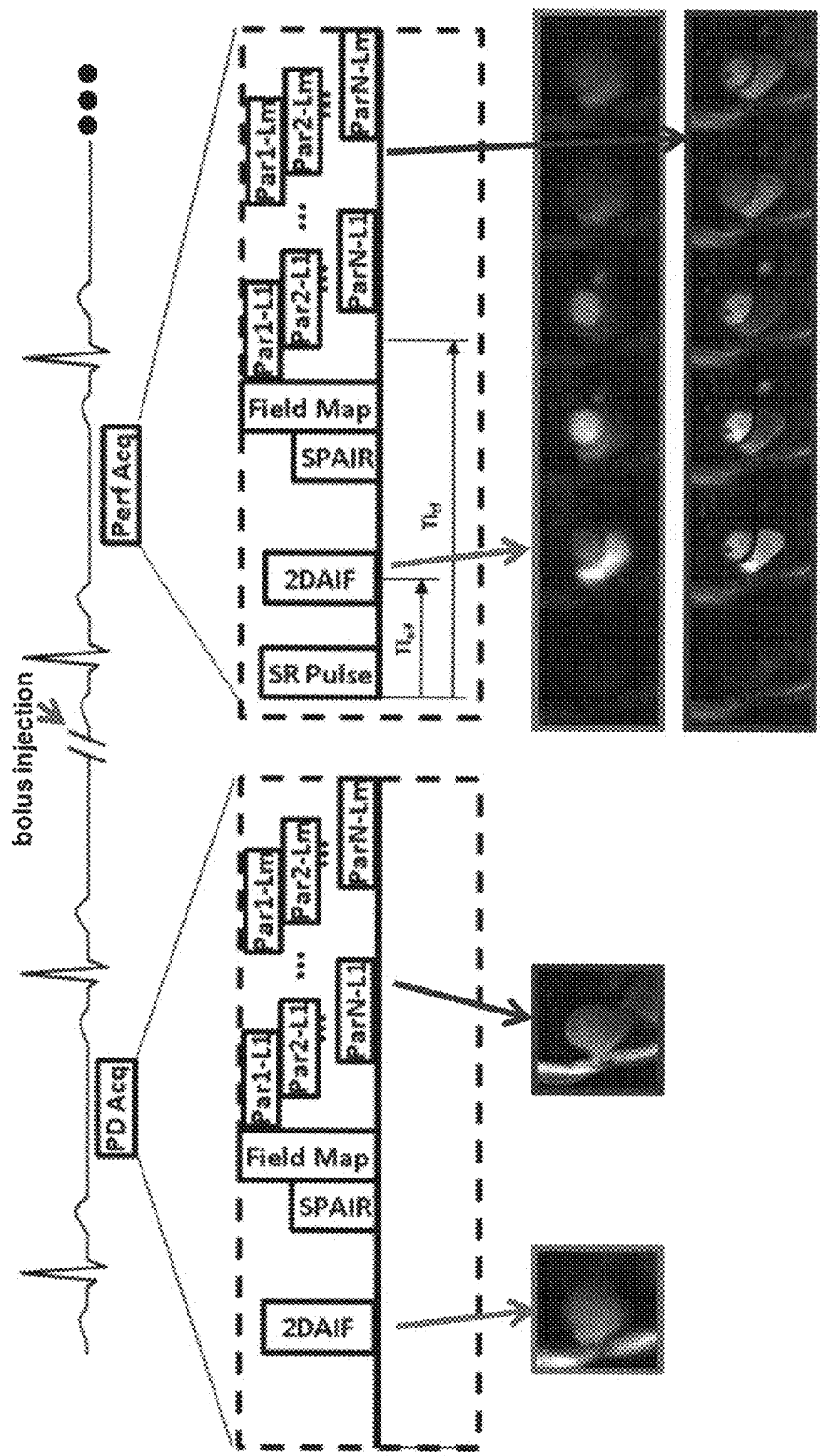
FIG. 4 is a sequence schematic for a dual sequence 3D stack-of-spirals (SoS) pulse sequence, according to one embodiment of the present disclosure.
Figure 5:
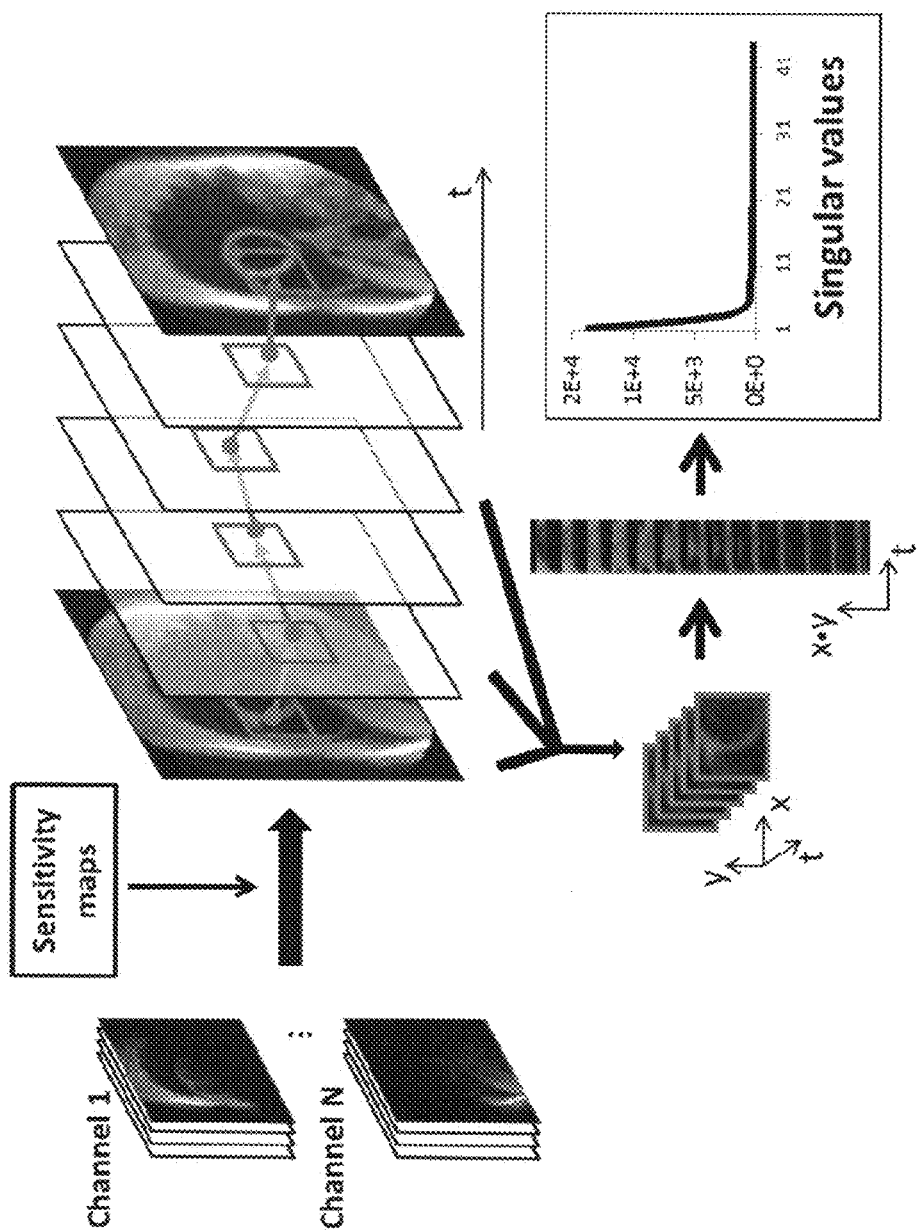
FIG. 5 shows a technique for image reconstruction used in one or more embodiments of the present disclosure.

FIG. 3 is a flow diagram illustrating operations of a method 300 for three-dimensional spiral perfusion imaging according to one embodiment of the present disclosure. At 302, an imaging pulse sequence with a three-dimensional stack-of-spirals trajectory is applied to acquire perfusion imaging data associated with the heart of a subject. At 304, perfusion images are reconstructed from the acquired perfusion imaging data, using parallel imaging and motion-guided compressed sensing. At 306, absolute perfusion values are determined, from the reconstructed perfusion images, based on time-intensity relationships, to quantify myocardial blood flow of the heart of the subject. At 308, a quantitative volumetric perfusion flow map is generated based on the determined absolute perfusion values.

In some embodiments, the acquiring of the perfusion imaging data (see 302) may be performed during first pass of a contrast agent. In some embodiments, the imaging pulse sequence may use a plurality of variable density spiral waveforms. In some embodiments, the variable density spiral waveforms may be used for each of a plurality of partitions configured such that volumetric image data for a whole ventricle or the whole heart of the subject is obtained. In some embodiments, the imaging pulse sequence may use spiral waveforms arranged in a linear stack. In some embodiments, the imaging pulse sequence may use spiral waveforms arranged in a spiral-radial configuration in which spiral planes are organized into a spherical pattern. In some embodiments, the spiral planes may be arranged with a random radial and azimuthal angle covering a sphere in k-space. In some embodiments, the imaging pulse sequence may use spiral interleaves that are uniformly spaced in the k-z direction with an angularly uniform pattern in time.

In some embodiments, acquiring the perfusion imaging data by the imaging pulse sequence (see 302) may include acquiring magnetic resonance data associated with the heart of the subject. In some embodiments, the parallel imaging and motion-guided compressed sensing (see 304) may use Block Low-rank Sparsity with Motion guidance (BLOSM) combined with sensitivity encoding (SENSE) ([2-4]). In some embodiments, determining the absolute perfusion values based on the time-intensity relationships (see 306) may include transforming a volumetric imaging dataset associated with the reconstructed perfusion images into a set of time-intensity curves. In some embodiments, the absolute perfusion values may be determined on a pixel-wise or segmental basis, from the time-intensity relationships, to quantify the myocardial blood flow. In some embodiments, determining the absolute perfusion values on the pixel-wise or segmental basis comprises using at least one of Fermi-function deconvolution ([5]), multi-compartment Kety modeling ([6]), distributed-parameter models, and model-independent deconvolution ([7]).

In some embodiments, the method 300 may further include acquiring one or more two-dimensional spiral images to quantify an arterial input function (AIF) for quantification of myocardial perfusion. In some embodiments, the method 300 may further include acquiring two-dimensional proton density (PD) images for normalization of an arterial input function (AIF) to convert signal intensity of acquired AIF images into gadolinium concentration to perform quantification of perfusion.

Further details of certain embodiments of the present disclosure will now be discussed. In some embodiments, perfusion imaging is performed using a dual sequence 3D stack-of-spirals pulse sequence (see e.g., FIG. 4). During the first few heart beats of acquisition, proton density weighted, 3D spiral datasets can be obtained for signal intensity normalization and calibration kernel images. In some embodiments these images can be used both for data collection and field-map generation for off-resonance correction of the perfusion imaging. A 2D proton density image for normalization of the arterial input function (AIF) can also be acquired. Following bolus injection of a contrast agent, 2D AIF images and 3D spiral acquisition can commence for a number of heart beats during first pass of the contrast agent. The AIF images can be acquired either following a SR preparation used for T1-weighting of the 3D images or can be acquired separately using a separate SR preparation with a short preparation time. In some embodiments, a spectrally selective adiabatic fat suppression (SPAR) pulse can be utilized to null fat at the acquisition of the center of k-space. In other embodiments, a spectral-spatial water excitation pulse can be used to selectively excite the water resonance while not exciting spins corresponding to fat.

In some embodiments, the spiral readouts utilized are variable density waveforms which can be used to flexibly modulate the sampling density, both to provide enhanced data for image registration and to generate an incoherent sampling pattern. In such embodiments, spiral interleaves can be uniformly spaced in the k-z direction with an angularly uniform sampling pattern of the spiral interleaves in time. In other embodiments, a randomized temporal sampling pattern of the interleaves (such as golden-angle in time) can be used in combination, to further improve incoherency of sampling. The angular sampling of the interleaves can either be changed for each interleaf (golden-angle in k-t) or just between repetitions of the 3D data collection for each heart beat in time (golden-angle in time). In other embodiments, to further improve efficiency, the density of the spiral waveforms can be modulated in the k-z direction, to further under-sample higher spatial frequencies, for example. Furthermore, the spacing and sampling of the spiral planes in the k-z direction can be modulated to both increase sampling efficiency and to further improve incoherency of sampling.

The spiral waveforms are not limited to a linear stack arrangement; in some embodiments, the spiral waveforms can be organized in a hybrid spiral-radial configuration wherein the spiral planes are organized into a spherical pattern. Also, completely random ordering of the spiral planes can be acquired with a random radial and azumthal angle. While some embodiments are timed to the cardiac cycle, it should be appreciated that given the sampling pattern and motion-compensated reconstruction, continuous acquisition may be performed so as not to require cardiac gating or breath-holding.

In some embodiments, image reconstruction may use parallel imaging and compressed sensing (CS) with motion-compensation, for example using Block Low-Rank Sparsity with Motion-Guidance (BLOSM) ([4]) combined with sensitivity encoding (SENSE) ([3]). In some embodiments of the present disclosure, BLOSM can be implemented for image reconstruction, to exploit matrix low-rank sparsity within motion-tracked regions from SENSE-combined images (see FIG. 5). In this technique, 2D blocks can be tracked in the stack of spirals that were first-fourier transformed in the k-z direction. In another embodiment 3D blocks can be tracked in the 3D image volume. Using BLOSM, sparsity and low rank in the singular value decomposition (SVD) domain are enforced over small image blocks. Other techniques can be used where the whole 3D volume or a sub-volume (i.e., region around the heart) may be tracked separately, in some embodiments. Additionally, the concept also extends to other possible combinations of motion-compensation and parallel imaging. The objective for such a reconstruction is to enable high quality images sets to be obtained even in the setting of significant respiratory motion (e.g., inability to hold breath, free-breathing) and cardiac motion (e.g., arrhythmia). Other techniques which may be used with aspects of the present disclosure in one or more embodiments for parallel imaging and compressed sensing may include one or more techniques described in U.S. Patent Application Publication No. 2015/0285889.

Following image reconstruction, 3D volumetric imaging datasets (see e.g., reconstructed perfusion images in FIG. 6) throughout the first pass of contrast agent are obtained. The datasets can then be transformed into a set of time-intensity curves (see e.g., FIG. 7), in units of gadolinium concentration, using Bloch model simulations ([8]).

The SR weighted image signal intensities (I) can be normalized by the proton density weighted image signal intensity ($I_{PD}$) and corrected for the difference between the flip angle for the saturation recovery image ($\alpha T1$) and the flip angle of the PD images ($\alpha_{PD}$) (Equation 1). Bloch equation simulation can be performed to determine the T1 relaxation time at each time point to determine the gadolinium (Gd) concentration (Equation 2). In this equation, TD is the delay from the saturation pulse to the first readout rf pulse, and TR is the time between readout rf pulses. The Bloch simulation accounts for the fact that multiple spiral trajectories may sample the center of k-space. After completion of this modeling, Gd(t) curves (see e.g., FIG. 7) can be created from the pre-contrast T1 ($T_{1pre}$) and the post contrast T1 images ($T_{1post}$) (Equation 3) for both the AIF and TF and can be used to determine perfusion. From these time-intensity curves, the absolute flow (perfusion) can be determined on a pixel-wise and/or segmental basis, using a number of methods such as, but not limited to, Fermi-function deconvolution ([5]), multi-compartment Kety modeling ([6]), distributed-parameter models, or model-independent deconvolution techniques ([7]). Furthermore, within the compressed sensing reconstruction framework, a term corresponding to a constraint based on these models may be incorporated to the reconstruction to directly create perfusion pixel maps from the underlying data.

$$S(x, y, t) = \frac{I(x, y, t)}{I_{PD}(x, y)} \cdot \frac{\sin(\alpha_{PD})}{\sin(\alpha_{T1})} \quad (1)$$

$$S(t) = \frac{\sum_{n=1}^{N}\left\{\left(1 - e^{-\frac{TD}{T(t)}}\right) \cdot \left[e^{-\frac{TR}{T(t)}} \cdot \cos(\alpha_{T1})\right]^{n-1} + \left(1 - e^{-\frac{TR}{T(t)}}\right) \cdot \frac{1 - \left[e^{-\frac{TR}{T(t)}} \cdot \cos(\alpha_{T1})\right]^{n-1}}{1 - e^{-\frac{TR}{T(t)}} \cdot \cos(\alpha_{T1})}\right\}}{\sum_{n=1}^{N}\left\{\left[e^{-\frac{TR}{T(t)}} \cdot \cos(\alpha_{PD})\right]^{n-1} + \left(1 - e^{-\frac{TR}{T(t)}}\right) \cdot \frac{1 - \left[e^{-\frac{TR}{T(t)}} \cdot \cos(\alpha_{PD})\right]^{n-1}}{1 - e^{-\frac{TR}{T(t)}} \cdot \cos(\alpha_{PD})}\right\}} \quad (2)$$

$$[Gd](t) = \frac{1}{r_1}\left(\frac{1}{T_{1post}(t)} - \frac{1}{T_{1pre}}\right) \quad (3)$$

Examples of practicing aspects of the present disclosure will now be described along with corresponding results and with reference to illustrations in FIGS. 4-9. Some experimental data is presented herein for purposes of illustration and should not be construed as limiting of the present disclosure in any way or excluding any alternative or additional embodiments. In one example implementation, imaging was performed in six subjects on a 1.5 T Siemens Avanto scanner during injection of 0.1 mmol/kg of Gd-DTPA. A 4× accelerated 3D SoS trajectory was used, with 3 variable density spirals per partition. Other parameters included: 50 rest perfusion images with 10 slices; FOV 320 mm²; thickness 8 mm; in plane resolution ~2 mm; $TI_{aif}$=10 ms; $TI_{tf}$=80 ms; TE=1.2 ms; Perfusion: $FA_{aif}$=45°, $FA_{tf}$=25°; PD: $FA_{aif}$=15°, $FA_{tf}$=5°; 5 ms RO, temporal window ~210 ms.

During the first few heart beats of acquisition, proton density weighted, 3D spiral datasets were obtained for signal intensity normalization and calibration kernel images. These images can be used both for data collection and field-map generation for off-resonance correction of the perfusion imaging. A 2D proton density image for normalization of the arterial input function (AIF) was also acquired. Following bolus injection of a contrast agent, single-shot, 2D slice acquisition of 2D AIF images and 3D spiral acquisition commenced for a number of heart beats during first pass of the contrast agent. The AIF images can be acquired either following the SR preparation used for T1-weighting of the 3D images or can be acquired separately using a separate SR preparation with a short preparation time. A spectrally selective adiabatic fat suppression ("SPAR") pulse was utilized to null fat at the acquisition of the center of k-space. The spiral readouts are variable density waveforms which can be used to flexibly modulate the sampling density, both to provide enhanced data for image registration and to generate an incoherent sampling pattern. Spiral interleaves are uniformly spaced in the k-z direction (denoted "Par1", "Par2" to "ParN" in FIG. 4) with an angularly uniform sampling pattern of the spiral leaves (denoted "L1" to "Lm" in FIG. 4) in time.

Figure 6:
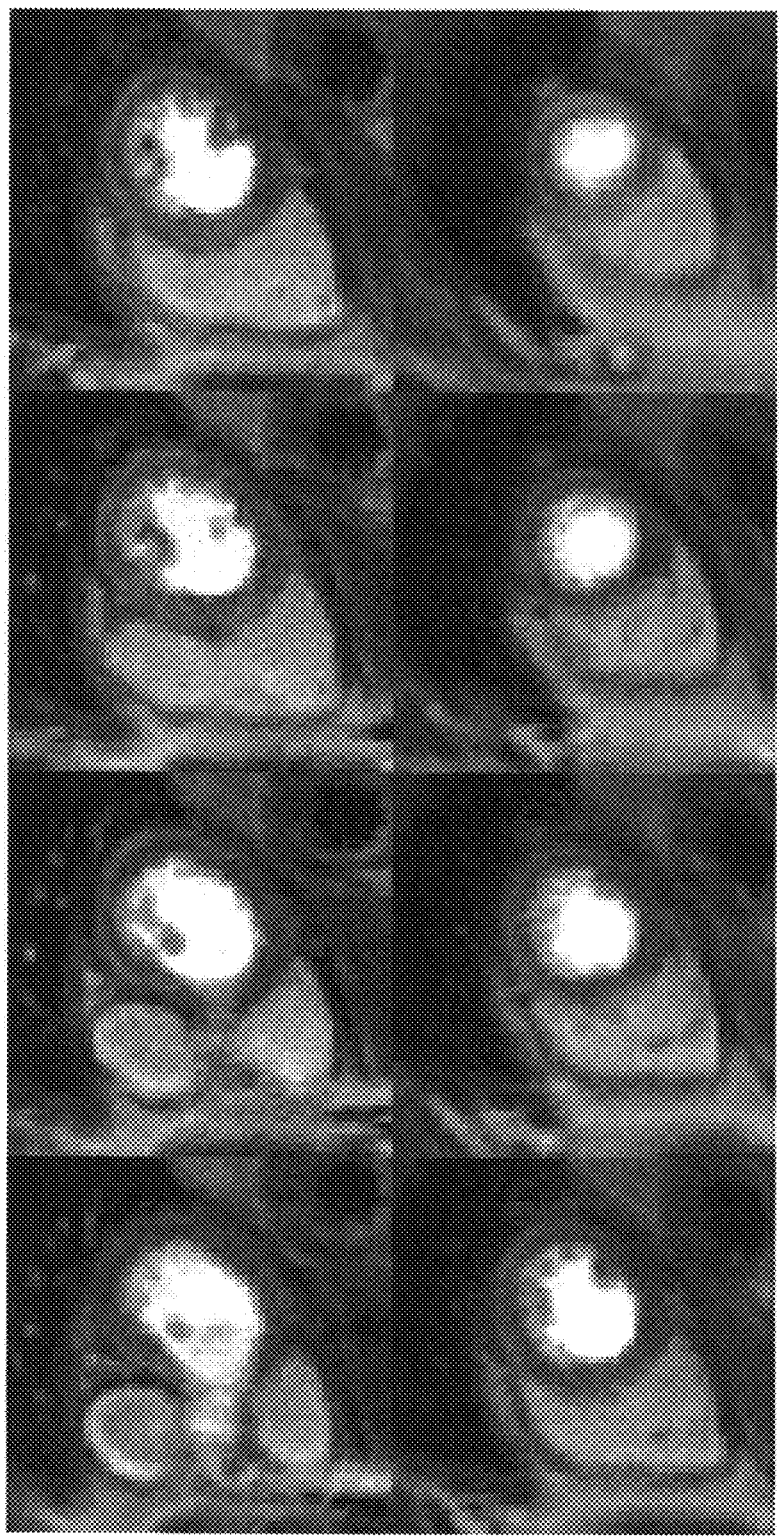
FIG. 6 shows reconstructed perfusion images, according to one embodiment of the present disclosure.
Figure 7:
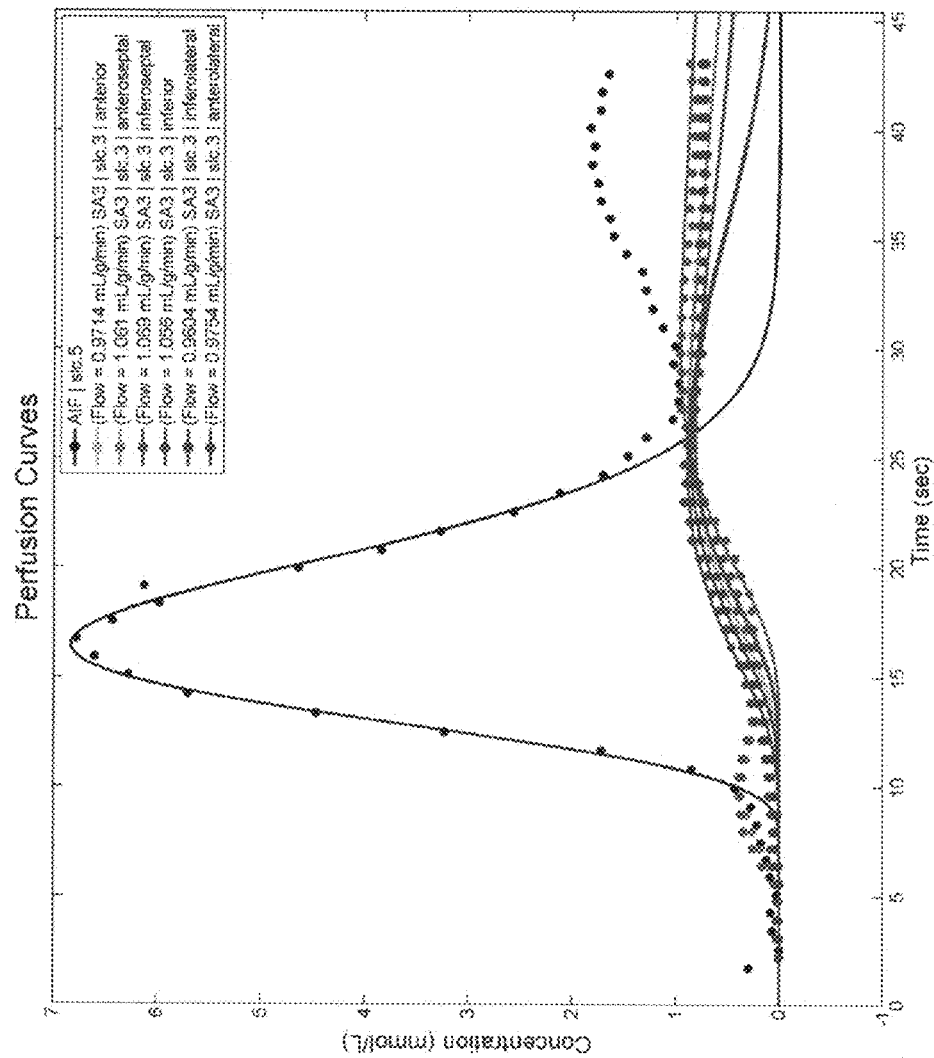
FIG. 7 shows time-intensity curves in units of gadolinium concentration, according to one embodiment of the present disclosure.
Figure 8:
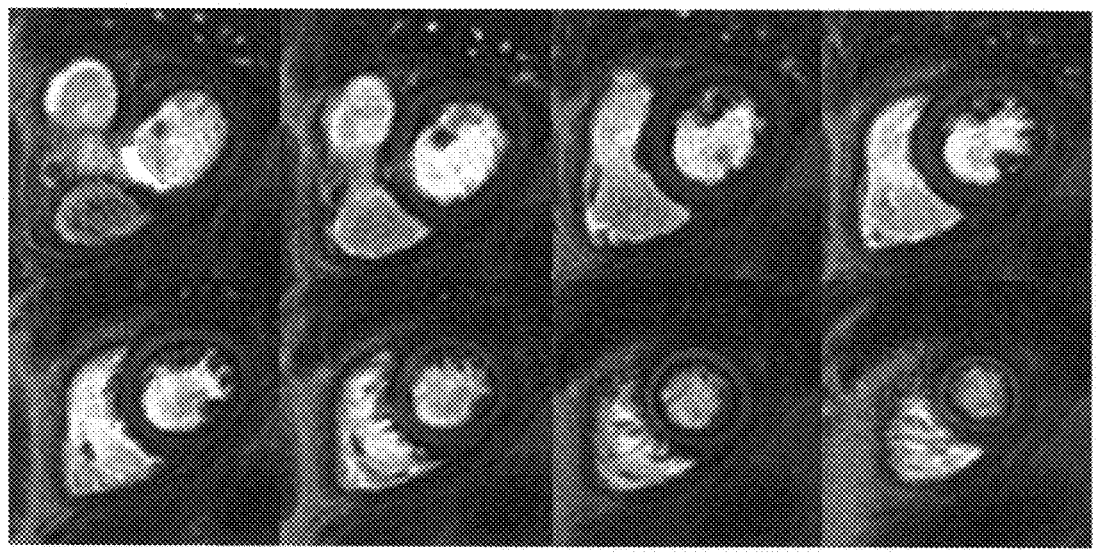
FIG. 8 shows a pixel wise myocardial perfusion flow map, according to one embodiment of the present disclosure.
Figure 9:
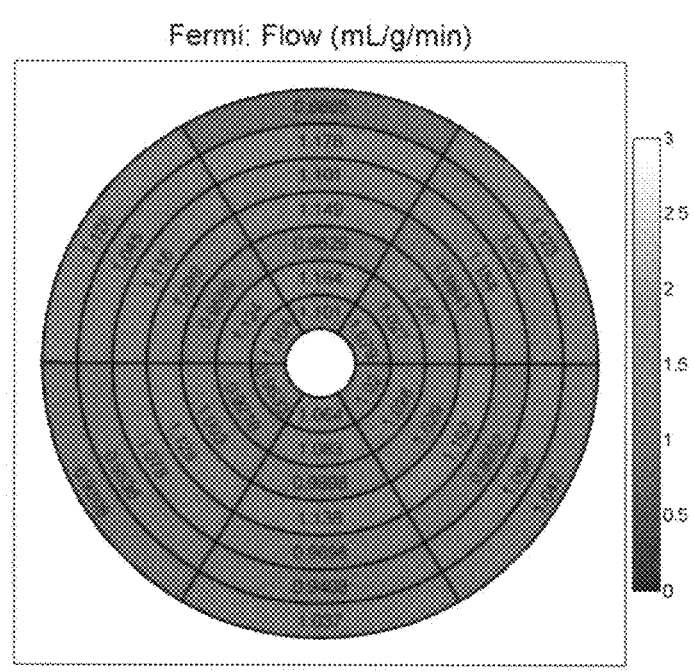
FIG. 9 shows a pixel wise myocardial perfusion flow map, according to one embodiment of the present disclosure.

From the image reconstruction, 3D volumetric imaging datasets throughout the first pass of contrast was obtained (see FIG. 6 perfusion images reconstructed using BLOSM combined with SENSE). The datasets were then normalized by the PD images and then Bloch model simulation was used to convert to a set of time-intensity curves (FIG. 7), in units of gadolinium concentration. From these time-intensity curves, the absolute flow (perfusion) was determined on a pixel-wise (FIG. 8) and segmental basis (FIG. 9) using Fermi-function deconvolution ([5]).

In comparison to conventional, previous approaches by others, the high SNR of a 3D approach in accordance with the embodiment of this example implementation provides for improvements over conventional techniques in reconstruction quality, and benefits pixel-wise perfusion quantification which can be limited by poor SNR. The motion guided BLOSM-SENSE reconstruction improves the robustness of perfusion imaging in the presence of respiratory motion. The results demonstrate successful application of 3D absolute quantitative first-pass myocardial perfusion imaging using stack-of-spirals in subjects. The sequence can generate robust quantitative pixel wise myocardial perfusion flow maps covering the entire ventricle, enabling absolute volumetric quantification of ischemic burden.

CONCLUSION

The specific configurations, choice of materials and the size and shape of various elements can be varied according to particular design specifications or constraints requiring a system or method constructed according to the principles of the present disclosure. Such changes are intended to be embraced within the scope of the present disclosure. The presently disclosed embodiments, therefore, are considered in all respects to be illustrative and not restrictive. The patentable scope of certain embodiments of the present disclosure is defined by the appended claims, and all changes that come within the meaning and range of equivalents thereof are intended to be embraced therein.

REFERENCE LIST

[1] Jerosch-Herold, M. Quantification of myocardial perfusion by cardiovascular magnetic resonance. *Journal of Cardiovascular Magnetic Resonance*, 12:57 (2010).
[2] Lustig et al. Sparse MRI: The application of compressed sensing for rapid MR imaging. *Magnetic Resonance in Medicine*, 58 (6):1182-1195 (2007).
[3] Pruessman et al. SENSE: Sensitivity encoding for fast MRI. *Magnetic Resonance in Medicine*, 42: 952-962 (1999).
[4] Chen et al. Motion-compensated compressed sensing for dynamic contrast-enhanced MRI using regional spatiotemporal sparsity and region tracking: Block low-rank sparsity with motion-guidance (BLOSM). *Magnetic Resonance in Medicine*, 72 (4): 1028-1038 (2014).
[5] Jerosch-Herold, M. et al. Magnetic resonance quantification of the myocardial perfusion reserve with a Fermi function model for constrained deconvolution. *Med Phys*. 1998 January; 25 (1):73-84.
[6] Tofts, P. S. et al. Estimating kinetic parameters from dynamic contrast-enhanced T(1)-weighted MRI of a diffusable tracer: standardized quantities and symbols. *J Magn Reson Imaging*. 1999 September; 10 (3):223-32.
[7] Jerosch-Herold M. et al. Myocardial blood flow quantification with MRI by model-independent deconvolution. *Med Phys*. 2002; 29:886-897.
[8] Cernicanu A. et al. Theory-based signal calibration with single-point T1 measurements for first-pass quantitative perfusion MRI studies. *Acad Radiol*. 2006; 13:686-693.

What is claimed is:

1. A method for perfusion imaging of a subject, comprising:
   acquiring perfusion imaging data associated with the heart of a subject, the acquiring comprising applying an imaging pulse sequence with a three-dimensional stack-of-spirals trajectory;
   reconstructing perfusion images from the acquired perfusion imaging data, wherein the reconstructing comprises parallel imaging and motion-guided compressed sensing;
   determining absolute perfusion values from the reconstructed perfusion images wherein the determining comprises transforming a volumetric imaging dataset associated with the reconstructed perfusion images into a set of time-intensity curves representative of time-intensity relationships; and
   generating a quantitative volumetric perfusion flow map based on the determined absolute perfusion values;
   wherein the absolute perfusion values are determined on a pixel-wise or segmental basis, from the time-intensity relationships, to quantify myocardial blood flow of the heart of the subject.

2. The method of claim 1, wherein the acquiring of the perfusion imaging data is performed during first pass of a contrast agent.

3. The method of claim 1, wherein the imaging pulse sequence uses a plurality of variable density spiral waveforms.

4. The method of claim 3, wherein the plurality of variable density spiral waveforms are used for each of a plurality of partitions configured such that volumetric image data for a whole ventricle or the whole heart of the subject is obtained.

5. The method of claim 1, wherein the imaging pulse sequence uses spiral waveforms arranged in a linear stack.

6. The method of claim 1, wherein the imaging pulse sequence uses spiral waveforms arranged in a spiral-radial configuration in which spiral planes are organized into a spherical pattern.

7. The method of claim 1, wherein the spiral planes are arranged with a random radial and azimuthal angle covering a sphere in k-space.

8. The method of claim 1, wherein the imaging pulse sequence uses spiral interleaves that are uniformly spaced in the k-z direction with an angularly uniform pattern in time.

9. The method of claim 1, wherein acquiring the perfusion imaging data by the imaging pulse sequence comprises acquiring magnetic resonance data associated with the heart of the subject.

10. The method of claim 1, wherein the parallel imaging and motion-guided compressed sensing uses Block Low-rank Sparsity with Motion guidance (BLOSM) combined with sensitivity encoding (SENSE).

11. The method of claim 1, wherein determining the absolute perfusion values on the pixel-wise or segmental basis comprises using at least one of Fermi-function deconvolution, multi-compartment Kety modeling, distributed-parameter models, and model-independent deconvolution.

12. The method of claim 1, further comprising acquiring one or more two-dimensional spiral images to quantify an arterial input function (AIF) for quantification of myocardial perfusion.

13. The method of claim 1, further comprising acquiring two-dimensional proton density (PD) images for normalization of an arterial input function (AIF) to convert signal intensity of acquired AIF images into gadolinium concentration to perform quantification of perfusion.

14. A system for perfusion imaging of a subject, comprising:
a data acquisition device configured to acquire perfusion imaging data associated with the heart of a subject, the acquiring comprising applying an imaging pulse sequence with a three-dimensional stack-of-spirals trajectory; and
one or more processors configured to:
reconstruct perfusion images from the acquired perfusion imaging data, wherein the reconstructing comprises parallel imaging and motion-guided compressed sensing,
determine absolute perfusion values from the reconstructed perfusion images, wherein the absolute perfusion values are determined by transforming a volumetric imaging dataset associated with the reconstructed perfusion images into a set of time-intensity curves representative of time-intensity relationships, and
generate a quantitative volumetric perfusion flow map based on the determined absolute perfusion values;
wherein the absolute perfusion values are determined on a pixel-wise or segmental basis, from the time-intensity relationships, to quantify the myocardial blood flow.

15. The system of claim 14, wherein determining the absolute perfusion values on the pixel-wise or segmental basis comprises using at least one of Fermi-function deconvolution, multi-compartment Kety modeling, distributed-parameter models, and model-independent deconvolution.

16. The system of claim 14, wherein the data acquisition device comprises a magnetic resonance imaging device.

17. The system of claim 14, wherein the acquiring of the perfusion imaging data is performed during first pass of a contrast agent.

18. The system of claim 14, wherein the imaging pulse sequence uses a plurality of variable density spiral waveforms.

19. The system of claim 18, wherein the plurality of variable density spiral waveforms are used for each of a plurality of partitions configured such that volumetric image data for a whole ventricle or the whole heart of the subject is obtained.

20. The system of claim 14, wherein the imaging pulse sequence uses spiral waveforms arranged in a linear stack.

21. The system of claim 14, wherein the imaging pulse sequence uses spiral waveforms arranged in a spiral-radial configuration in which spiral planes are organized into a spherical pattern.

22. The system of claim 14, wherein the spiral planes are arranged with a random radial and azimuthal angle covering a sphere in k-space.

23. The system of claim 14, wherein the imaging pulse sequence uses spiral interleaves that are uniformly spaced in the k-z direction with an angularly uniform pattern in time.

24. The system of claim 14, wherein acquiring the perfusion imaging data by the imaging pulse sequence comprises acquiring magnetic resonance data associated with the heart of the subject.

25. The system of claim 14, wherein the parallel imaging and motion-guided compressed sensing uses Block Low-rank Sparsity with Motion guidance (BLOSM) combined with sensitivity encoding (SENSE).

26. The system of claim 14, wherein the data acquisition device and one or more processors are further configured to acquire one or more two-dimensional spiral images to quantify an arterial input function (AIF) for quantification of myocardial perfusion.

27. The system of claim 14, wherein the data acquisition device and one or more processors are further configured to acquire two-dimensional proton density (PD) images for normalization of an arterial input function (AIF) to convert signal intensity of acquired AIF images into gadolinium concentration to perform quantification of perfusion.

28. A method for magnetic resonance imaging of a subject, comprising:
acquiring magnetic resonance data associated with an area of interest of a subject, the acquiring comprising applying an imaging pulse sequence with a three-dimensional stack-of-spirals trajectory;
reconstructing images corresponding to the area of interest from the acquired magnetic resonance data, wherein the reconstructing comprises parallel imaging and motion-guided compressed sensing using Block Low-rank Sparsity with Motion guidance (BLOSM);
quantifying, from the reconstructed images, values associated with a physiological activity in the area of interest, wherein the quantifying is based on time-intensity relationships; and
generating, from the quantified values, a quantitative volumetric map representing the physiological activity;
wherein the values are determined on a pixel-wise or segmental basis, from the time-intensity relationships, to quantify myocardial blood flow.

29. The method of claim 28, wherein the physiological activity comprises a fluid flow in the area of interest.

30. The method of claim 28, wherein the area of interest of the subject comprises at least a part of the heart of the subject.

31. The method of claim 30, wherein the quantified values associated with the physiological activity area associated with absolute perfusion values.

32. The method of claim 28, wherein quantifying the values using the time-intensity relationships comprises transforming a volumetric imaging dataset associated with the reconstructed images into a set of time-intensity curves.

33. The method of claim 28, wherein generating the quantitative volumetric map comprises generating a volumetric perfusion flow map based on the quantified values.

34. The method of claim 28, wherein the acquiring of the magnetic resonance data is performed during first pass of a contrast agent introduced in the area of interest.

35. The method of claim 28, wherein the imaging pulse sequence uses a plurality of variable density spiral waveforms.

36. The method of claim 35, wherein the plurality of variable density spiral waveforms are used for each of a plurality of partitions configured such that volumetric image data for the entire area of interest is obtained.

37. The method of claim 28, wherein the imaging pulse sequence uses spiral waveforms arranged in a linear stack.

38. The method of claim 28, wherein the imaging pulse sequence uses spiral waveforms arranged in a spiral-radial configuration in which spiral planes are organized into a spherical pattern.

39. The method of claim 28, wherein the spiral planes are arranged with a random radial and azimuthal angle covering a sphere in k-space.

40. The method of claim 28, wherein the imaging pulse sequence uses spiral interleaves that are uniformly spaced in the k-z direction with an angularly uniform pattern in time.

41. The method of claim 28, wherein determining the absolute perfusion values on the pixel-wise or segmental basis comprises using at least one of Fermi-function deconvolution, multi-compartment Kety modeling, distributed-parameter models, and model-independent deconvolution.

42. The method of claim 28, further comprising acquiring one or more two-dimensional spiral images to quantify an arterial input function (AIF) for quantification of myocardial perfusion.

43. The method of claim 28, further comprising acquiring two-dimensional proton density (PD) images for normalization of an arterial input function (AIF) to convert signal intensity of acquired AIF images into gadolinium concentration to perform quantification of perfusion.

44. A non-transitory computer-readable medium having stored instructions that, when executed by one or more processors, cause a computing device to perform functions that comprise:

acquiring perfusion imaging data associated with the heart of a subject, the acquiring comprising applying an imaging pulse sequence with a three-dimensional stack-of-spirals trajectory;

reconstructing perfusion images from the acquired perfusion imaging data, wherein the reconstructing comprises parallel imaging and motion-guided compressed sensing;

determining absolute perfusion values from the reconstructed perfusion images, wherein the determining comprises transforming a volumetric imaging dataset associated with the reconstructed perfusion images into a set of time-intensity curves representative of time-intensity relationships; and generating a quantitative volumetric perfusion flow map based on the determined absolute perfusion values;

wherein the absolute perfusion values are determined on a pixel-wise or segmental basis, from the time-intensity relationships, to quantify myocardial blood flow of the heart of the subject.

* * * * *